United States Patent [19]

Cegielski et al.

[11] Patent Number: 5,159,924
[45] Date of Patent: Nov. 3, 1992

[54] METHOD AND APPARATUS FOR SELECTIVELY MIXING GASES

[76] Inventors: Michael J. Cegielski, 2404 Temescal, Norco, Calif. 91760; Teunis T. van den Berg, 24699 Moondshadow Dr., Marino Valley, Calif. 92387

[21] Appl. No.: 592,271
[22] Filed: Oct. 3, 1990
[51] Int. Cl.$^5$ .............................................. A61M 15/00
[52] U.S. Cl. ........................ 128/203.12; 128/203.25; 128/205.24
[58] Field of Search ............... 128/203.12, 203.25, 128/204.18, 205.11, 205.24

[56] References Cited

U.S. PATENT DOCUMENTS

| | | | |
|---|---|---|---|
| 258,677 | 2/1952 | Marrett | 128/203.12 |
| 3,351,057 | 11/1967 | Goodyear | 128/203.12 |
| 3,896,837 | 7/1975 | Rohling | 137/110 |
| 4,266,573 | 5/1981 | Braatz | 137/630.18 |
| 4,576,159 | 3/1986 | Hahn | 128/203.14 |
| 4,606,340 | 8/1986 | Ansite | 128/205.24 |

FOREIGN PATENT DOCUMENTS

2166360 5/1986 United Kingdom .

Primary Examiner—Edgar S. Burr
Assistant Examiner—Aaron J. Lewis
Attorney, Agent, or Firm—Knobbe, Martens, Olson & Bear

[57] ABSTRACT

A mixing device for respiratory, therapeutic, or anesthetic uses provides two of three gases to a mixed gas outlet. A gas selecting means fluidly connected with a first and second gas supplies selectively provides fluid passage of only one of the first or second gases to the outlet. A gas bypass selectively bypasses two of the three gases to the gas outlet. A locking device activated by the selecting means prevents a predetermined one of the first or second gases from being bypassed to the gas outlet. A first and second pressure balancing regulator equalizing the pressures of the selected gas and the third gas before passing those gases to a controllable mixing device which meters the gases into a mixing chamber, after which the gases are passed to the gas outlet. Advantageously, a gas selector knob is positioned coaxially with a mixing valve such that rotation of the selector valve causes correctly calibrated scales to become visible to reflect the mixture of the selected gases as they are mixed.

26 Claims, 6 Drawing Sheets

METHOD AND APPARATUS FOR SELECTIVELY MIXING GASES

FIELD OF THE INVENTION

This invention relates to gas control apparatus, particularly those used with ventilators for therapeutic treatment of patients with respiratory problems, and more particularly relates to a medical gas mixer for selecting gases to be mixed while maintaining the accuracy of the resulting mixture over a specified range, independent of inlet pressure fluctuation.

BACKGROUND OF THE INVENTION

For various medical reasons, patients are often put on mechanical or electronic ventilators which provide air, oxygen, or a mixture of air and oxygen to the patient. The gas mixture concentration is usually expressed as a percentage of oxygen. In surgery or for pain control, sometimes a mixture of oxygen and nitrous oxide is provided to the patient. Sometimes, gases other than nitrous oxide will be used, such as anesthetics. If an anesthetic or nitrous oxide is provided, it is important to accurately know the concentration of the gas provided to safeguard the health of the patient.

Thus, for example, U.S. Pat. No. 3,351,057 to Goodyear discloses an anesthesia apparatus which supplies oxygen, anesthesia or a combination of both, with a toggle mechanism which shuts off one gas supply and connects the device to ambient air in the event the oxygen supply is inadvertently shut off. The mechanism described, however, is complex and it requires the patient to draw the ambient air into the system.

Another patent, U.S. Pat. No. 3,896,837 to Rohling, discloses a gas mixing apparatus for respirators and medical devices with a gas bypass arranged such that when the pressure in a mixed gas delivery line drops below a predetermined pressure, a bypass valve opens to permit direct passage of an inlet gas, or to permit passage of a third gas from a gas tank. In Rohling, however, there is no regulation control on the added gas which can lead to an unknown mixture of gasses being delivered to the patient.

Continuous flow gas metering devices are known in the art For example, U.S. Pat. No. 4,266,573 to Braatz discloses an anesthesia machine for providing a mixture of oxygen and a second gas, such as nitrous oxide, in selected proportions. Each of the two gasses pass through separate needle valve metering assemblies which are interconnected so that when a predetermined ratio of nitrous oxide and oxygen is achieved, the percentage of oxygen may not be further diminished, thereby safeguarding the health of the patient. However, the needle valve assemblies are complex, and pressure variations can affect the relative flow rates.

Another gas metering device uses pulsed solenoid control valves, as described in U.S. Pat. No. 4,576,159 to Hahn. However, the pulsed valve actuation causes pressure surges which are so severe that specially designed mixing chambers must be used which dampen the pressure fluctuations of the mixed gases. The pressure fluctuation and pulsed gas disbursement can also lead to inaccuracies in the relative gas concentrations in the mixed gas.

SUMMARY OF THE INVENTION

The present invention relates to an improved gas mixing device which provides an accurate mixture of several gases. This invention allows the operator to select one of two gases for mixing with a third gas. Advantageously, the third gas is a sustaining gas such as oxygen, and one of the first two gases which, while potentially hazardous, has beneficial properties in controlled mixtures with other gases, such as nitrous oxide would when mixed with oxygen.

An important feature of this invention is that its design is intended to prevent a hazardous gas from being inadvertently supplied to the patient if the source of a sustaining gas, which is being mixed with the hazardous gas, inadvertently fails.

Another advantage of this invention is that it is constructed so that if two non-hazardous gases are being mixed and supplied to the patient, such as air and oxygen, then the bypass feature allows provision of either mixed gas in the event one of the supplies for the non-hazardous mixed gases inadvertently fails.

Another significant feature of this invention is an inter-locking feature to further prevent the inadvertent passage of a predetermined one of the first two selected gases, such as a hazardous gas, from being bypassed directly to the patient in the event of a supply failure of the mixed gas.

A further feature of this invention is the positive positioning of a selector knob coaxially with a mixing knob. The selector knob allows the operating personnel to select the desired gases for mixing, while the mixing knob controls the mixture of the selected gases. To prevent inadvertent passage of a hazardous gas to the patient when the selection knob is inadvertently set in a position which could select either of two gases, one of which is hazardous, a return device urges the selector knob to select the non-hazardous gas and to lock out the hazardous gas from being bypassed directly to the patient.

A further advantage of the coaxial knob is that it is configured to enable the mixtures of the selected gases to be read off the knob no matter which of the first two gases are selected for mixing with the third gas. The selector knob is configured so that it switches scales depending upon which of the two gases are selected, with the selected scale moving with the mixing knob. The scales are advantageously calibrated in terms of percentage concentration relative to the third gas, which gas is usually oxygen.

This invention allows easy selection of two of three gases for mixing, by use of two coaxial knobs, with one knob selecting the gases for mixing, and a second knob selecting the mixture of the gases. The gas selector knob also advantageously actuates the safety inter-lock to prevent passage of a hazardous gas directly to a gas outlet going to a patient.

DESCRIPTION OF THE DRAWINGS

The above, and other, objects and advantages of the present invention will be better understood from the description of the preferred embodiment as given below, taken in conjunction with the drawings in which like reference characters or numbers refer to like parts throughout the description, and in which.

DESCRIPTION OF THE PREFERRED EMBODIMENT

Figure 1:
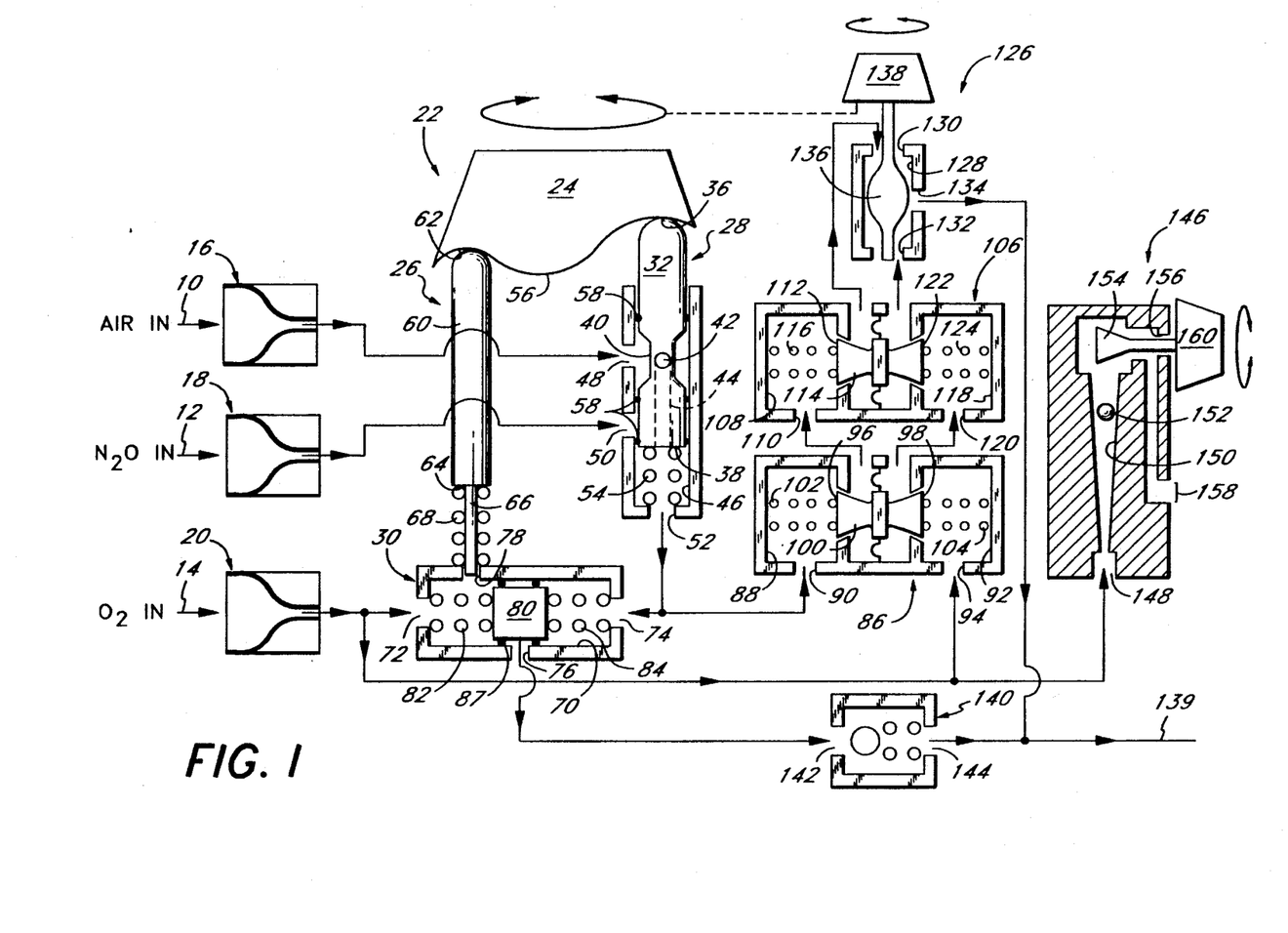
FIG. 1 is a schematic illustration of this invention.
Figure 2:
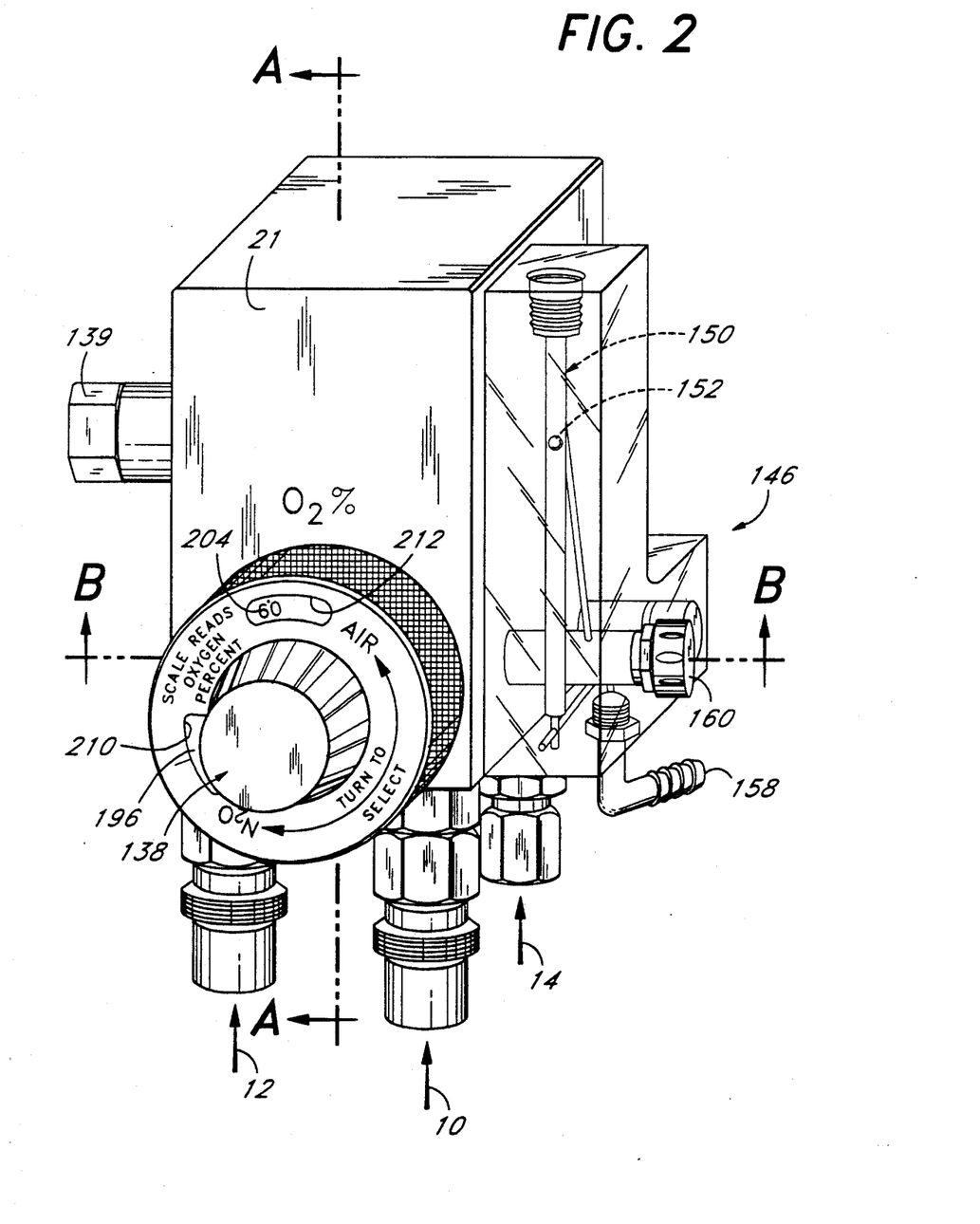
FIG. 2 is a perspective view of an embodiment of the invention.
Figure 3:
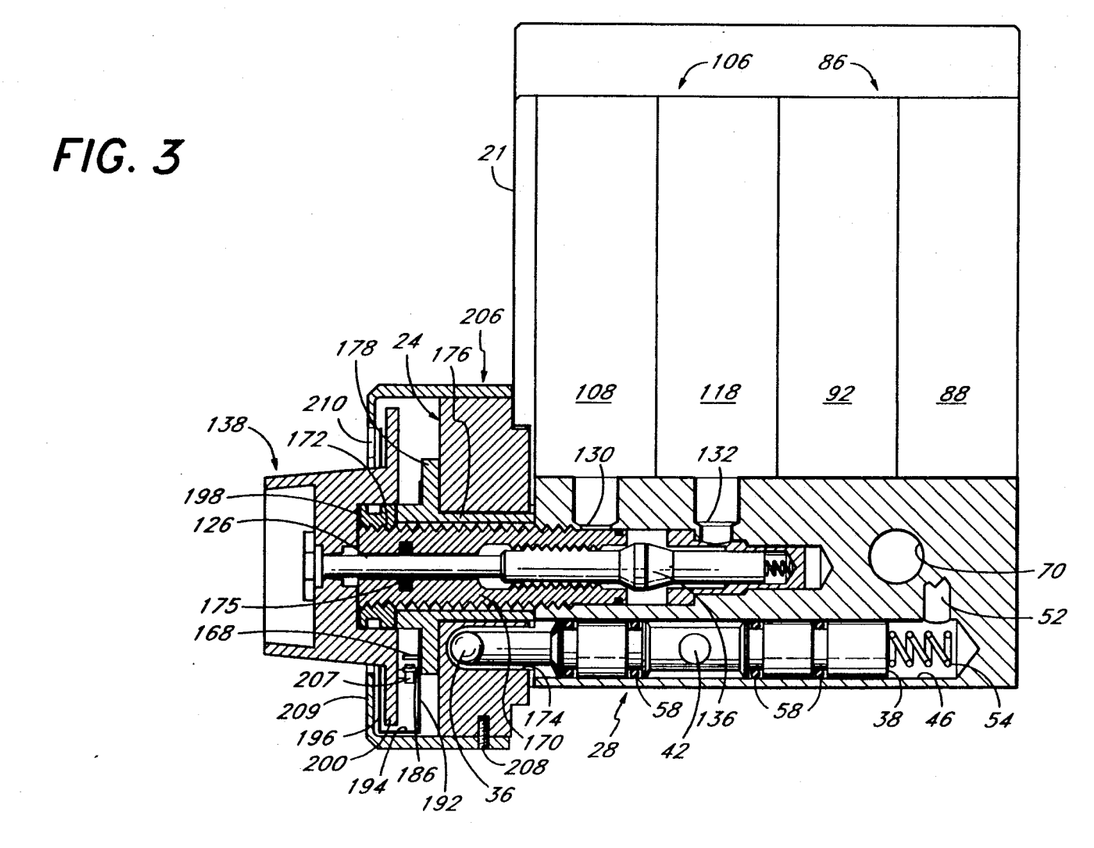
FIG. 3 is a sectional view taken along A—A of FIG. 2.
Figure 4:
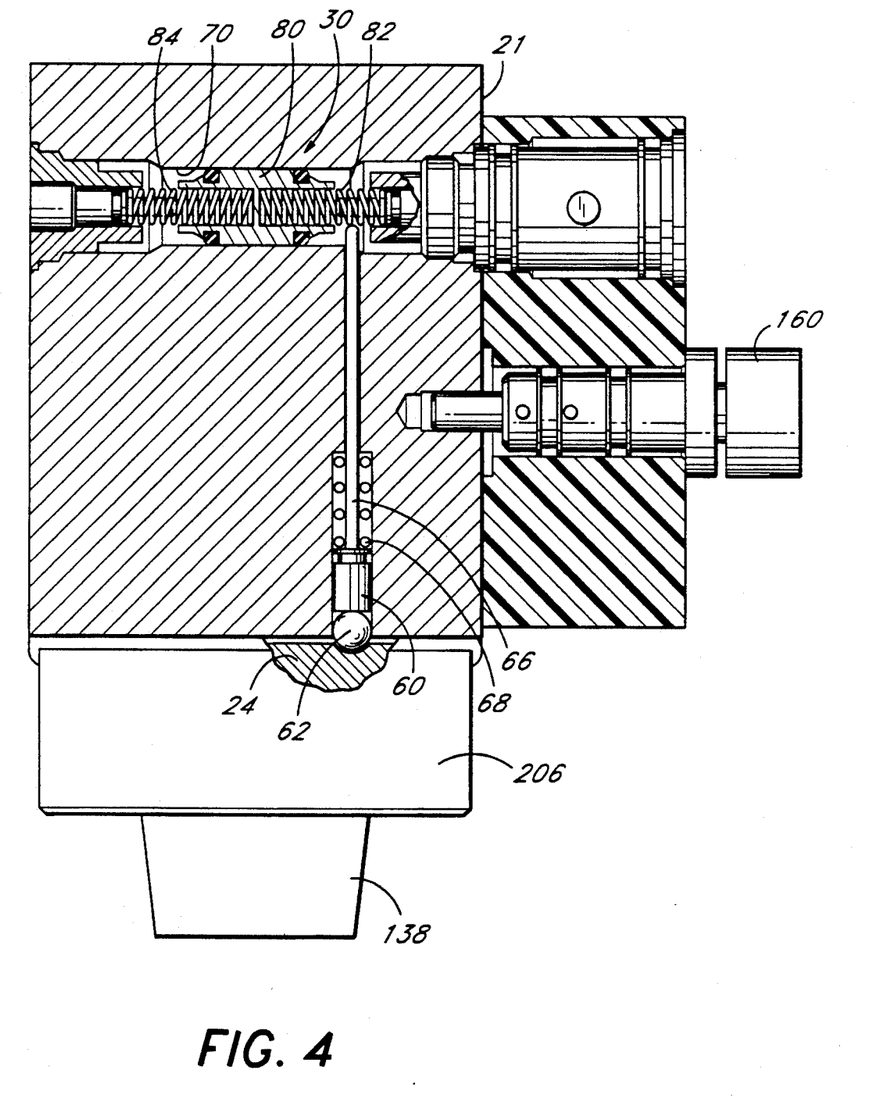
FIG. 4 is a sectional view taken along B—B of FIG. 2.

The preferred embodiment is best understood by referring to the schematic of FIG. 1. FIGS. 2-4 show a physical embodiment of the invention. Given the following disclosure and the drawings, one skilled in the art could determine various ways to configure the fluid passages to provide the required fluid communication. Thus, to make the figures easier to understand, many of the fluid communication pathways are not shown in FIGS. 2-4.

Referring to FIGS. 1 through 4, but primarily to FIGS. 1 and 2, a plurality of gas sources are illustrated as comprising a first gas source 10, a second gas source 12 and a third gas source 14. Preferably, the first gas source 10 comprises a source of pressurized air, while the second gas source 12 comprises a source of pressurized nitrous oxide, and the third gas source 14 comprises a source of pressurized oxygen. These preferred gas sources 10, 12, 14 are commonly available sources of pressurized gas in hospitals.

The gas sources 10, 12, 14 are in fluid communication with means for providing one-directional flow from the respective gas sources such as check valves, or preferably, duckbill, c.v. 30 micron filters, 16, 18 and 20, respectively. The fluid connections between the gas sources 10, 12 and 14, and the duckbills 16, 18 and 20 are of conventional types known in the art, and preferably comprise male and female DISS fittings, NIST fittings, or other gas fittings.

A housing 21 (FIG. 2) contains a selector valve assembly 22 (FIG. 1), to which the duckbills 16, 18 respectively are fluidly connected. The valve assembly 22 comprises a selector valve control knob 24, a safety inter-lock 26 (FIGS. 1 and 4) and a gas selector piston assembly 28 (FIGS. 1 and 3). Duckbill 20 (FIG. 1) connected to the third gas source 14, is in fluid communication with a bypass valve assembly 30 (FIGS. 1 and 4) also contained in housing 21 (FIG. 2).

Referring primarily to FIGS. 1 and 3, the gas selector piston assembly 28 will be referred to as a gas selector or gas selector assembly, and comprises a cylindrical member such as a plunger or piston 32 having a first contoured end 36 and opposite thereto a second, substantially flat end 38 which is oriented perpendicular to the longitudinal axis of the piston 32. Advantageously, the end 36 is spherical, and preferably comprises a rotating ball. A recessed area 40 is located intermediate the ends 36, 38, with the recessed area 40 having a smaller diameter than the cylindrical plunger or piston 32, and extending substantially around the circumference of piston 32. A first aperture 42 extends radially inward from the outer surface of the recessed area 40, towards the longitudinal axis of the cylindrical piston 32. A second aperture 44 extends along the longitudinal axis of the piston 32, between the first aperture 42 and the flat end 38. The apertures 42, 44 form a gas passage from the recess 40 to the end 38 of piston 32.

The piston 32 is mounted in a generally cylindrical chamber 46 so that the plunger can reciprocate along the longitudinal axis of the piston 32. Inlet ports 48, 50 open into the chamber 46, and are in fluid communication with the first and second gas supplies 10, 12, respectively, through duckbills 16, 18, respectively. An outlet port 52, opens into chamber 46, with the outlet port 52 being in fluid communication with the recess 40 through the first aperture 42 and the second aperture 44. A resilient member, such as coil spring 54, is located between an end of the chamber 46 and the flat end 38 so as to resiliently urge the spherical end 36 of the piston 32 against a contoured or cammed surface 56 on the gas selector control knob 24. Sealing means, such as O-rings 58, are located on opposite sides of the recess 40 to seal the piston 32 against the walls of the chamber 46.

The piston 32 is slidably positioned in chamber 46 by the contoured surface 56 to define alternate fluid communication passages with the gas sources 10, 12 through inlet ports 48, 50, respectively. For example, when the piston 32 is positioned with the recessed area 40 adjacent the inlet port 48, then a fluid passage is formed from the first gas source 10, through the check valve 16, through the inlet port 48, to the recessed area 40, through the first and second apertures 42, 44, and out the outlet 52. Similarly, when the piston 32 is positioned with the recessed area 40 adjacent the inlet port 50, then a fluid passageway is formed from gas source 12, through check valve 18, inlet port 50, recess 40, apertures 42 and 44, and outlet port 52. The piston 32 may be positioned so that either the first gas source 10 or the second gas source 12 is directed to the exit port 52, but does not permit both the first and second gas sources 10 and 12 to be simultaneously in fluid communication with the exit port 52. There is thus provided means for selectively communicating gases to an outlet from one of two gas sources.

The piston 32 is spring-loaded by coil spring 54 so as to urge the piston 32 into a position which delivers the first gas (air) instead of the second gas (nitrous oxide). Thus, in the event the knob 24 is only partially rotated so as to not definitively select the second gas, the piston 32 will be urged into the position to select only the first gas (air).

Referring to FIGS. 1 and 4, the safety inter-lock 26 comprises a generally cylindrically-shaped member such as push rod 60, having a first contoured end 62, and opposite thereto a substantially flat end 64 oriented substantially perpendicular to the longitudinal axis of the push rod 60. Advantageously, the end 62 is spherical, and preferably comprises a rotating ball. A smaller diameter cylindrical member such as stop pin 66 extends along the longitudinal axis of the push rod 60 from the flat end 64. Resilient means, such as coil spring 68 surrounds the stop pin 66 and urge the end 62 of push rod 60 against the contoured surface 56 of the knob 24.

Still referring to FIGS. 1 and 4, the bypass valve assembly 30 comprises a chamber 70 and a first inlet port 72, which is in fluid communication with the third gas source 14 through the check valve 20. A second inlet port 74 is located at the end of the chamber 70, opposite the inlet port 72. The inlet port 74 is in fluid communication with the outlet port 52 of gas selector 28. Located intermediate the inlets 72, 74 is an outlet 76, which also communicates with the inside of the chamber 70. Located intermediate the inlets 72, 74 is an aperture 78 into the chamber 70, which is positioned closer to the inlet 72 than to the inlet 74, and is further positioned so that stop pin 66 may extend through the aperture 78.

A piston 80 is slidably mounted inside the chamber 70, with resilient means, such as coil springs 82, 84, being located on opposite ends of the piston 80 to urge the piston 80 towards a neutral position. Sealing means, such as O-rings 87, are located on opposite ends of the piston 80 so as to provide a substantially gas-tight fit between the piston 80 and the adjacent walls of the chamber 70. In the neutral position, piston 80 and sealing means 87 cooperate to block the exit port 76 so as to prevent the flow of the third gas through the outlet port 76, and also prevent the flow of either the first or second gases from the outlet port 52 through the inlet port 74 and outlet port 76.

Referring to FIGS. 1 and 3, but primarily to FIG. 1, a first balancing regulator 86 is in fluid communication with the third gas source 14 and with the outlet port 52 of the selector valve 22. The balancing regulator 86 substantially equalizes the pressures of the gases flowing through the regulators. The balancing regulator 86 is described in more detail in U.S. Pat. No. 3,895,642, and comprises a first chamber 88 having an inlet port 90 which is in fluid communication with the outlet port 52 of selector valve assembly 22. The balancing regulator 86 has a second chamber 92, having an inlet port 94 which is in fluid communication with the third gas source 14. First and second chambers 88, 92 contain valve seats 96, 98, respectively. A two-seated valve 100 is located intermediate the first second and second chambers 88, 90, and is mounted such that in a neutral position, it is located equidistant from, but not seated against, valve seats 96, 98 to define a substantially equal fluid flow path from both the first and second chambers 88, 92, respectively. The two seated valve 100 may advantageously comprise two separate balls seating against two separate valve seats. Resilient means, such as coil springs 102, 104, located in chambers 88, 92, respectively, communicate with opposite ends of valve 100 and urge the valve 100 to maintain this neutral position.

The valve 100 has sufficient area in each of the first and second chambers 88, 92 such that a pressure differential in one of the chambers will exert sufficient force on the valve 100 and cause it to open one of the valve seats 96, 98, and close the other of the valve seats. Thus, a higher pressure in one of the chambers 88, 92 will cause a reduced flow area between the respective valve seat 94 or 96 and the valve 100 to cause a reduction in the volume of gas passing through the higher pressure chamber, while simultaneously causing an increase in the amount of gas flowing between the valve 100 and the adjacent valve seat 96 or 98 in the opposite, lower pressure chamber. The result is that an increase in pressure causes a reduction in the exit area while causing an increase in the exit area of the opposite chamber so that the volume of gas exiting both of the chambers tends to approach one another.

The balancing regulator 86 can equalize the pressures of the gases exiting from chambers 88, 92, to within about 1%, and can accommodate about 20 pounds per square inch (psi) of pressure differential. A pressure differential greater than 20 psi, will cause the valve 100 to completely seat and prevent all flow of gas from the high pressure chamber. Similarly, if no gas enters one of the chambers 88, 92, the valve 100 will seat completely in the chamber containing gas so as to effectively prevent any gas flow through the regulator 88.

Preferably, a second balancing regulator 106 is placed in fluid communication with the first balancing regulator 86. Thus, the second balancing regulator 106 has a first chamber 108 containing an inlet port 110 which is in fluid communication with the first chamber 88 of the first balancing regulator 86, through the space between the valve seat 96 and the valve 100 of the first balancing regulator 86. The first chamber 108 contains a valve seat 112 into which a mating valve 114 extends, with resilient means such as coil spring 116, urging the valve 114 toward the valve seat 112. The space between the valve seat 112 and valve seat 114 defines an exit port from the first chamber of the second balancing regulator 86.

Similarly, a second balancing regulator 106 contains a second chamber 118 containing an inlet port 120 in fluid communication with the second chamber 92 of the first balancing regulator 86 through the space between the valve 100 and the valve seat 98. The chamber 118 has a valve seat 122 surrounding a portion of the dual-sided valve 114, and with resilient means such as coil spring 124, urging the valve 114 toward the valve seat 122. The springs 116, 124 are balanced so that in a neutral position, a space is defined between valve seats 112, 122 and the adjacent portions of the valve 114 so as to define equally sized exit flow paths from the chambers 108 and 118. As with the valve 100 in the first balancing regulator 86, the two seated valve 114 may comprise two separate balls seating against two separate valve seats. The use of two balancing regulators 86, 106, equalizes the pressure of the gases flowing through them to about 0.1%.

Referring to FIGS. 1 and 3, a mixing valve 126 is in fluid communication with the gases exiting from the second balancing regulator 106, or if the second balancing regulator is not used, with the first balancing regulator 86. The mixing valve 126 comprises a chamber 128 having a first inlet port 130, a second inlet port 132, and an outlet port 134. The first inlet port 130 is in fluid communication with the gases exiting from the first chamber 108 of the second balancing regulator 106. The second inlet port 132 is in fluid communication with the gases exiting from the second chamber 118 of the second balancing regulator 106. A flow varying member such as mixing valve poppet 136 extends through the mixing chamber 128 and has a portion extending through the first and second inlets 130, 132. One end of the mixing valve poppet 136 is connected to a knob or dial 138. The dial 138 contains scales allowing operating personnel to read the oxygen concentration, as described in more detail later. As described later in FIG. 5, the dial 138 is coaxial with knob 24.

The mixing valve 126 is assembled such that rotation of the mixing knob, or dial 138 causes the amount of gases passing through the first and second inlets to vary in a predetermined manner such that rotation of the dial 138 allows a predetermined mixture of gases to be selected The poppet 136 translates between two valve seats to vary the areas of inlets 130, 132 so as to increase the flow area of inlet 130 while decreasing the flow area of inlet 132, and vice versa. Advantageously the two metered gases may be mixed within the mixing valve 126 and then exit through outlet port 134 to a gas outlet 139 (see FIG. 2).

The gases exiting from outlet port 134 are in fluid communication with the patient (not shown) by means known in the art such as ventilators, respirators, etc., none of which are described or illustrated herein.

In an alternate embodiment of this invention, the outlet 76 of the bypass valve assembly 30 is in fluid communication with a unidirectional flow means such as a duckbill, or a bypass check valve 140 as shown in FIG. 1, which in turn is in fluid communication with gas outlet 139.

A first normal operational flow path is thus defined from the gas sources 10, 12, through the selector valve assembly 22, through balance regulators 86, 106, through mixing valve 126, to the gas outlet 139. A second normal operational flow path is defined from the third gas source 14, through balance regulators 86, 106, through mixing valve 126, to the gas outlet 139. A first, failsafe bypass flow path is defined for the gas source 10, through the bypass valve assembly 30, through outlet 76, and through the bypass check valve 140, to the gas outlet 139. Gas source 12, the hazardous gas in the illustrated embodiment, has no bypass system. A second, failsafe bypass flow path is defined for the gas source 14, through the bypass valve assembly 30, through outlet 76, and through the bypass check valve 140, to the gas outlet 139. The first and second, failsafe bypass flow paths become functional only when a predetermined pressure differential is applied to gas bypass valve 30, with the bypass flow paths being operational in only one direction via the duckbills 16, 18, 20, or if present, the check valve 140.

Referring to FIGS. 1 and 2, but primarily to FIG. 1, a metering/bypass valve assembly 146 has an inlet port 148 which is in fluid communication with the third gas inlet 20. The bypass valve 146 comprises a tapered or converging cavity 150 which contains a visible ball to movably obstruct the cavity and form a flow meter 152. The position of the visible ball 152 indicates the flow rate. The flow meter 152 is known in the art and is thus not described in detail herein.

A valve 154, and valve seat 156 are located intermediate the flow meter 152, and a second gas outlet 158. The valve 154 has one end connected to a valve knob 160, with the valve 154 being mounted in the bypass valve 146 such that rotation of the valve knob 160 causes the valve 154 to move relative to the valve seat 156 in order to vary the amount of gas passing from the inlet 148, to the second outlet 158.

Referring primarily to FIG. 1, the operation of the gas mixer will now be described The disclosed apparatus provides for one of two predetermined gases may be mixed with a third gas. Alternately phrased, the apparatus provides for the successive mixing of two gases from three separate pressurized gas supplies 10, 12, and 14, with one of the gases being selected from a predetermined combination of two of the three gases. The operation will be described with respect to the preferred gases which are air, nitrous oxide, and oxygen. A person rotates knob 24 to select a gas from one of gas supplies 10 or 12 (air or nitrous oxide), with the selected gas being mixed with the third gas 14 (oxygen). A scale on knob or dial 138 is calibrated so that the relative concentrations are illustrated, thus allowing operational personnel to readily select the desired mixture of gases by rotation of knob 138.

Rotation of the control knob 24 of the selector valve assembly 22 causes the cammed surface 54 to position both the cylindrical push rod 60, and the piston 32. Positioning the piston 32 will cause one of the first or second gases, either air or nitrous oxide, but not both, to pass through the gas selector 28 and exit through the exit port 52.

Alternately phrased, as the first and second gases from sources 10, 12, respectively, are exposed to the selector valve assembly 22, rotation of the control knob 24 causes the cammed surface 54 to contact the piston 32, thereby disposing the piston 32 relative to the first and second inlet ports 48, 50, of the selector valve assembly 22 so as to permit passage of either the first or second gas to the outlet 52 of the selector valve assembly 22.

The selected gas, illustrated in FIG. 1 as being air, is fluidly communicated to the bypass valve assembly 30, and also fluidly communicated to the first balancing regulator 86. The select gas passes through the first balancing regulator 86, through the second balancing regulator 106, and then into the first inlet 130 of mixing valve 126. The third gas source 14, which in this case is oxygen, provides the third gas to both the bypass valve assembly 30, and also to the inlet 94 of the first balancing regulator 86. The third gas passes through the first chamber 92 of the first balancing regulator 86, through the second chamber 118 of the second balancing chamber 108, and then into the inlet 132 of mixing valve 126. The balancing regulators 86, 106, equalize the pressure between the two gases passing through those regulators. The mixing valve 126 controls the mixtures of the two gases by varying the aperture area through which the two gases flow at substantially the same pressure. The metered gases then pass to the gas outlet 139 and to the patient through a respirator, etc.

The third gas 14 may be controllably provided directly to the patient through outlet 158, with the flow rate of the third gas being determined by the flowmeter 146, to which the third gas is also connected.

When the knob 24 is positioned so that piston 32 selects the second gas, nitrous oxide, then the cammed surface 56 simultaneously causes the push rod 60 to move downward against resilient member 68 such that stop pin 66 extends through the aperture 78 and prevents the piston 80 from moving into a position which would allow nitrous oxide to pass through the bypass valve 30 via second inlet 74 and outlet 76. As the gas passing from the bypass valve 30 through outlet port 76 goes to the gas outlet 139, the safety inter-lock 26 prevents the second gas, such as nitrous oxide, from being delivered to the patient through the bypass valve 38 in the event there is a failure of the third gas supply 14. There is thus provided a means for preventing a predetermined gas (second gas) of the first and second gas from being bypassed directly to the gas outlet 139, and thus passed directly to the patient.

The third gas source 14 which supplies oxygen is in fluid communication with the bypass valve assembly 30, with the first balancing regulator 86, and with the bypass valve assembly 30. In the event the selected gas passing through the exit port 52 of the gas selector 28 fails, then the gas pressure at the inlet 72 will exert a sufficient force on the slidable piston 80 so as to overcome the resistance of spring 84 thereby causing the piston 80 to uncover the exit port 76 and allow the third gas (oxygen) to pass through the bypass valve 30, through bypass check valve 140, and to the gas outlet 139. Thus, the bypass valve assembly 30 ensures a supply of the third gas to the gas outlet 139 in the event the gas supply selected by the selector valve assembly 22 is terminated or exhausted.

In a similar manner, if the gas selected by the selector valve assembly 22 is the first gas, namely air, then the safety inter-lock device 26 does not inhibit movement of the piston 80, and if the third gas supply 14 fails, then the first gas is bypassed directly to the outlet 139 via bypass valve 30.

On the other hand, if the gas selected by the selector valve assembly 22 is the second gas, the predetermined hazardous gas (nitrous oxide), then the safety inter-lock device 26 is activated by cam surface 56 so as to inhibit movement of piston 80, and thus prevents the bypass valve 30 from directly bypassing the second gas directly to the patient in the event of a failure of the third gas 14. Further, in the event the selected mixture of gases is the second gas (nitrous oxide) and the third gas (oxygen), then the balance regulators 80, 106, would shut down the flow of the second gas (nitrous oxide) to the patient in the event the third gas source 14 fails.

Figure 5:
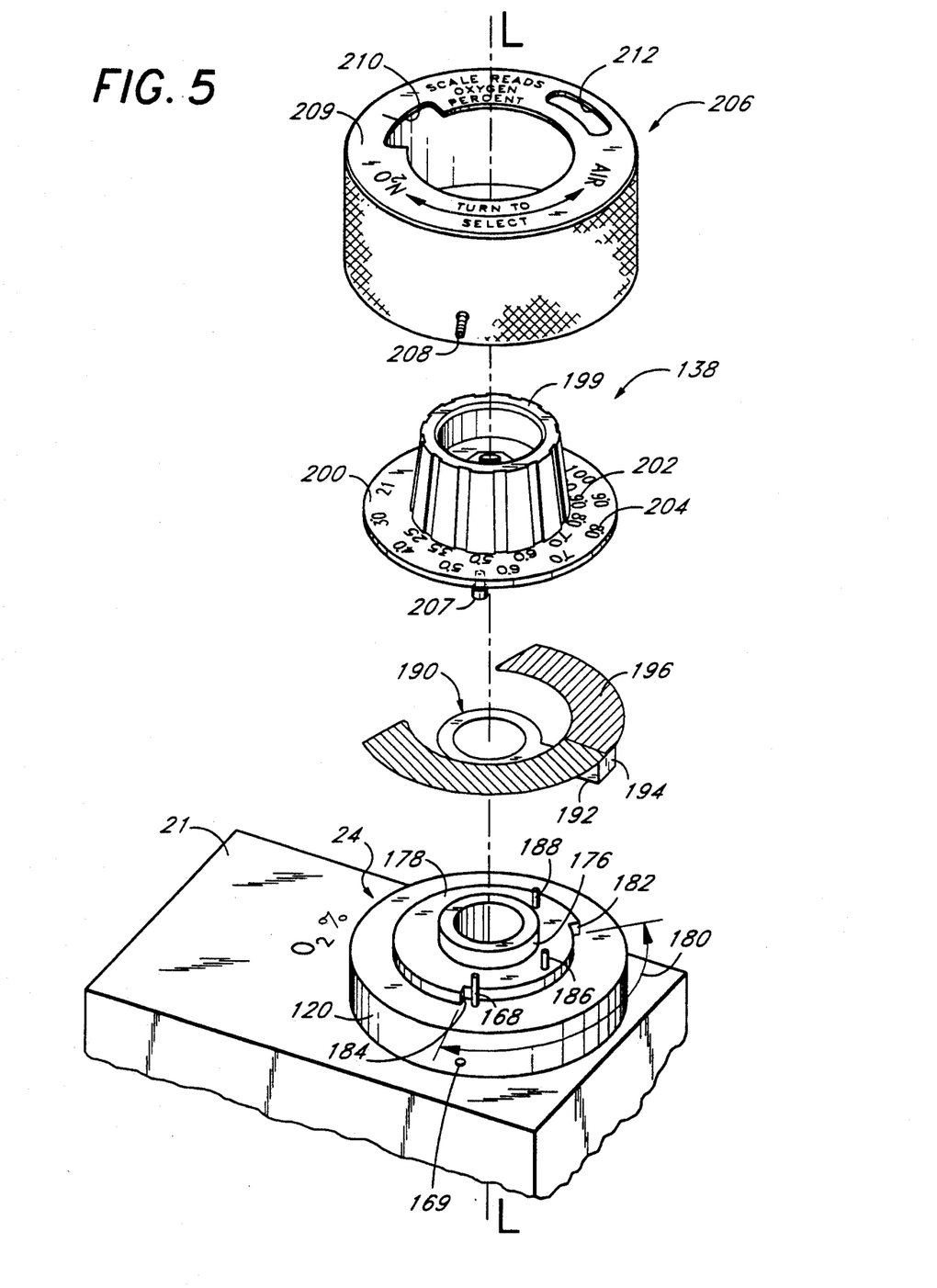
FIG. 5 is an exploded perspective view of a control knob of this invention.

Referring to FIGS. 2, 3, and 5, but primarily to FIGS. 3 and 5, an interconnection between the knobs 24 and 138 will be described. The knob 24 comprises a circular disk having a central hole through which the mixing member 136 extends. The line L—L in FIG. 5 is along the longitudinal axis of mixing member 136. The knob 24 rotates about line L—L, and abuts against the housing 21.

A stop pin 168 extends from the knob 24, along an axis substantially aligned with the longitudinal axis of mixing member 136. A threaded recess 169 (FIG. 5) is formed in the radial periphery of the knob 24. A tube 170 surrounds the mixing member 136, and has a first, exterior threaded end 172 (FIG. 3) extending through the hole in the knob 24. The mixing member 136 is sealed inside the tube 170 by an O-ring 175.

Figure 6:
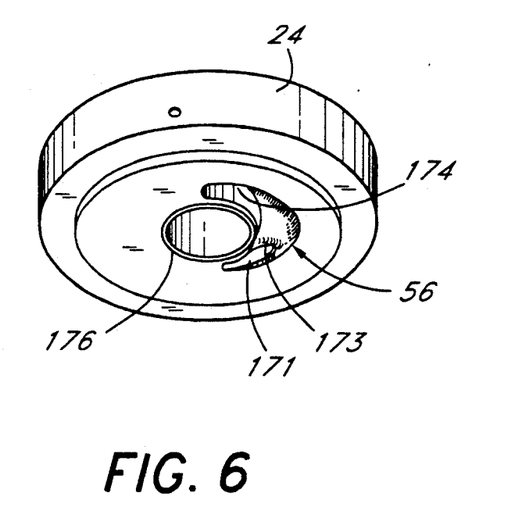
FIG. 6 is a perspective view of a control knob showing a cammed surface.

Referring to FIG. 6, the bottom of knob 24 contains the cammed surface 56, which is illustrated as comprising a slot having a curved, semicircular axis. The cammed surface 56 advantageously comprises a first slot 171 extending into the knob 24 at a first slope at a fixed radius from the center of the knob 24. The first slot 171 ends at a detente, such as a raised portion or ridge 173. The ridge is below the surrounding surface of the knob 24.

A second slot 174 begins at the ridge 173 and extends further into the knob 24 at a second slope along the same radius as that of the first slot 171. The slope of the second slot 174 is greater than the slope of the first slot 171. It is believed advantageous to have the slopes of the slots 171, 174 be non-linear, and increase as the depth of the slot increases.

Also as illustrated in FIGS. 3 and 6, the bottom surface of the knob 24 contains a recessed area around the periphery, forming a recessed lip which fits into a recessed area in the housing 21 (FIG. 3) to help hold the knob 24.

Referring to FIGS. 3 and 5, a flanged tube 176 surrounds a portion of the threaded end 172, with the tube 176 fitting inside the hole in the knob 24 so the knob 24 may rotate relative to the tube 176. One end of the flanged tube 176 removably engages the housing 21 in such a manner that the tube 176 is restrained from rotation Such engagement could comprise projections on the tube 176 fitting into slots in the housing 21, but such connecting means are known and not illustrated.

A flange 178 is located intermediate the ends of the tube 176, and extends radially outward. The flange 178 abuts the surface of the knob 24. A segment of the radial periphery of the flange 178 has a reduced radius to form a recessed area 180 in the outer periphery of the flange 178, with first and second shoulders 182, 184 at opposite ends of the recessed area 180. The recessed area subtends an arc of about 120 degrees.

The pin 168 is placed radially outward from the center of the knob 24 such that when the flange 178 abuts knob 24, the pin 168 can fit within the recessed area 180 and move between the first and second shoulders 182, 184, respectively, as knob 24 rotates relative to the flange 178.

A second pin 186 is placed on the flange 178, slightly to one side of the center of the recessed area 180, and just radially inward from the recessed area. The pin 186 is substantially aligned with the longitudinal axis of mixing member 136. A third pin 188 is placed on the flange 178, at the same radial distance as second pin 186, and aligned with the second pin 186. The third pin 188 is located about 30 degrees counterclockwise from the first shoulder 182. As the pins 184, 186 are connected to the non-rotating flanged tube 176, neither the second pin 184 nor the third pin 186 rotate.

When the flange 178 is assembled to abut knob 24, the pins 168, 186, and 188 are aligned along the same longitudinal axis. The lengths of the pins 168, 186, 188 are such that all of the pins end at about the same distance from the surface of the knob 24.

A semi-circular shield 190 abuts against the end of the flanged tube 176. The shield is best seen in FIG. 5 as comprising a radially extending arm 192, an axial offset arm 194, and a semicircular shield portion 196 substantially parallel to the arm 192. The shield portion 196 is color coded, having a yellow portion (for air) and a blue portion (for nitrous oxide) for the illustrated embodiment. The pin 168 does not contact the shield 190, as the flanged tube 176 holds the shield sufficiently away from the end of the pin 168 (FIG. 3).

A threaded fastener such as nut 198 threadably engages the threaded first end 172 of tube 170, and fastens the shield 190 between the nut 198 and the flanged tube 176. The nut 198 has a hole through which one end of the mixing member 136 extends, with the nut containing an O-ring seal to provide friction with the knob 138.

The knob 138 is fastened to the end of the mixing member 136. The knob 138 has an axial portion 199, and a radial flange 200 on which visible indicia, such as numbers, are placed. The numbers are advantageously calibrated relative to the device of this invention to reflect the percentage concentration of a selected gas being mixed.

In the illustrated embodiment, the numbers are calibrated relative to the third gas, oxygen, and thus visually display the percentage of oxygen. Advantageously, there are two sets 202, 204, of such calibrated numbers on the flange 200. The first set of numbers 202 is located radially inward on the flange 200, and reflects the percentage of the third gas (oxygen) when mixed with the second gas (nitrous oxide in the illustrated embodiment). The second set of numbers 204 reflects the percentage of the third gas (oxygen) when mixed with the first gas (air in the illustrated embodiment).

Depending from the flange 200 is a projection 207. The projection is illustrated as a screw, although it may be more economical to mold a ridge-like projection 207 integrally with the flange 200. The projection 207 is dimensioned and radially positioned on the flange 200, so that projection 207 can contact the ends of pins 168, 186, and 188 (FIG. 3).

A cap or cover 206 fits over the knob 138, and is connected by diverse means, such as set screw 208 (FIG. 5), so as to move with the knob 24. The cover 206 has a radially extending portion 209 containing a central aperture through which the axial portion of knob 138 extends. A first window 210 is formed in the radial portion 209 of cover 206 at a first radial distance. A second window 212 is also formed at a second radial distance in the radial portion 209. The first set of numbers 202 may be viewed through the first window 210. The second set of numbers 204 may be viewed through the second window 212.

When assembled, the shield portion 196 is located between the radial portion 209 of cover 206 and the radial flange 200 of the knob 138. The shield 190 is preferably made out of flexible plastic, which facilitates the assembly.

As previously described, rotation of the knob 24 selects one of the first or second gases 10, 12, to be mixed with the third gas 14, and in some circumstances engages safety lock 26 (FIG. 1). FIG. 5 illustrates a configuration in which the second gas 12 (nitrous oxide) is selected for mixing with the third gas 14 (oxygen). In this configuration, the cammed surface 56 on the bottom of knob 24 (FIG. 1) engages the safety lock 24 while simultaneously selecting the second gas 12 by gas selector assembly 28 (FIG. 1). The cammed surface 56 (FIG. 1) has detentes which inhibit movement of the ends 36 and 62 (FIG. 1) out of the selected position, and which urge the knob 24 to remain in this position until knob 24 this physically rotated.

As the cover 206 rotates with the knob 24, the rotation simultaneously selects which set of calibrated data is to be viewed through the windows 210, 212. As cover 206 rotates, the windows 210, 212 rotate relative to shield portion 196, so that one of the windows 210, 212 is always covered. For example, the first window 210 may be covered by shield portion 196, but the second set of numbers 204 may be read through the second window 212. Conversely, when the second window 212 is blocked by shield portion 196, the first set of numbers 202 may be read through the first window 210. There is thus provided means for changing calibrated scales to correspond to the selection of the gases being mixed with the same operation that selects the gases to be mixed or blended.

Once a particular gas is selected for mixing via the knob 24, then the knob 138 determines the particular blend of gases. The knob 138 is directly connected to the mixing member 136, so that rotation of knob 138 directly affects the mixture of the gases as described previously. However, a specified rotation of the knob 138 may cause different concentrations of the third gas (oxygen in the illustrated embodiment) which is being displayed. Thus one scale may need to rotate further than another scale. To accommodate this difference, variable rotational stop means are provided.

In the illustrated embodiment, the variable stop means comprise the pins 186 and 188, and the projection 207 on knob 138, although pin 168 may be used to inhibit motion. Referring to FIGS. 1, 5, and 6, FIG. 5 illustrates a configuration in which the second gas 12 (nitrous oxide) is selected for mixing with the third gas 14 (oxygen). In this configuration, the cammed surface 56 on the bottom of knob 24 (FIG. 1) engages the safety lock 24 while simultaneously selecting the second gas 12 by gas selector assembly 28 (FIG. 1). Also in this configuration, the end 36 of selector valve assembly 28 (FIG. 1) rests in the end of the first slot 171 adjacent the detente ridge 173 (FIG. 6). The end 62 of safety lock 26 (FIG. 1) is out of the slots 171, 174 (FIG. 6), and thus forced into a locking position to inhibit movement of piston 80 (FIG. 1).

The detente ridge 173 cammed surface 56 (FIG. 1) has detentes which inhibit movement of the ends 36 and 62 (FIG. 1) out of the selected position, and which urge the knob 24 to remain in this position until knob 24 this physically rotated.

Referring to FIGS. 3 and 5, the first pin 168 is forced against the shoulder 184 of recess 180 as the knob 24 is rotated so as to select the second gas 12 and third gas 14 (FIG. 1) for mixing. The first pin 168 and the third pin 188 limit rotation of the knob 138 as the depending projection 207 will hit the pins 168, 188 and be inhibited from further rotation. The knob 138 is allowed to rotate about 150 degrees between pins 168, 188 when in the position illustrated in FIG. 5.

While the pin 168 cannot rotate past shoulder 184, the pin 168 is restrained from rotation in the opposite direction only by the force of end 36 of the gas selector valve 28 (FIG. 1) being urged into the detente at the end of slot first slot 171 in knob 24 (FIG. 6) by the spring 54 and by the pressure of the gas on the cylindrical member 32 (FIG. 1). This force, in addition to the force to urge the end 36 (FIG. 1) over the ridge 173 inhibits movement of the pin 168 by the projection 207.

This increased resistance to further rotation can be perceived by an operator turning knob 138. This increased resistance also occurs as the oxygen concentration starts going below about 21% oxygen, the amount found in normal air. The increased resistance serves to notify the personnel operating the gas blender that little oxygen is being directly passed to the patient.

When the cover 206 and knob 24 are rotated so the pin 168 is against the first shoulder 182, then the end 36 (FIG. 1) is in the end of the second slot 174 (FIG. 6) and the end 62 (FIG. 1) is in the end of the first slot 171 (FIG. 6). In this position, the first gas 10 (air) has been selected for mixing with the third gas 14 (oxygen). Movement of knob 24 rotates the pin 168 between the two stationary pins 16, 188, which stop the rotation of knob 138 when projection 207 hits the pins 186, 188.

As the cover 206 and knob 24 are rotated to place the pin 168 against the shoulder 182, the second window is moved from above the shield portion 196 so the second set of numbers 204 may be read through the second window 212. Simultaneously, the first window 210 is moved over the shield portion 196 to prevent the first set of numbers 202 from being read through the first window 210.

The shield portion 196 may be color coded to further indicate which gas is being transmitted. For example, if the gas selected is nitrous oxide, the second gas 12, then the portion of the shield 196 displayed through the second window 212 may be blue to indicate nitrous oxide is being mixed. Conversely, if air is selected, the color yellow may be displayed through the first window 210.

There is thus advantageously provided means for changing calibrated scales to correspond to the selection of the gases being mixed while simultaneously selecting the gas to be mixed. There is further provided means for shutting off the passage of a selected (hazardous) gas if an operator attempts to select a gas mixture providing an undesirable concentration of a specified gas.

We claim:

1. A mixing device for respiratory or therapeutic use which mixes two gases from three separate pressurized gas supplies containing at least one sustaining gas and one harmful gas, while preventing the patient from inadvertently receiving a flow of harmful gas in the event the supply of the sustaining gas inadvertently fails, comprising:

a selector valve having a first inlet port fluidly connected to a first gas supply, a second inlet port fluidly connected to a second gas supply, one of the first or second gas supplies containing a harmful gas, and a selector valve outlet port, the selector valve configured to selectively permit fluid passage of only one of the first or second gas supplies to the selector valve outlet port;

a bypass valve having a first inlet port fluidly connected to a third gas supply, a second inlet port fluidly connected to the selector valve outlet port, and a bypass valve outlet port, the bypass valve configured to permit the third gas to flow to the bypass valve outlet port when the pressure of the third gas exceeds the pressure of the selected gas by a predetermined amount, the bypass valve being further configured to permit a predetermined one of the first or second gases to flow to the bypass valve outlet port when the pressure of the predetermined gas is greater than the third gas;

a first balancing regulator having a first inlet port and a first outlet port in fluid communication, a second inlet port and a second outlet port in fluid communication, the first balancing regulator inlet port being in fluid communication with the selector valve outlet port and to the bypass valve inlet port, and with the second inlet port of the first balancing regulator being in fluid communication with the third gas supply, the first balancing regulator providing a substantially equal gas pressure at the first and second outlet ports when the selected gas and the third gas are communicated to the balancing regulator, the balancing regulator preventing passage of the higher pressure gas when the pressure differential at the balance regulator between the selected gas and the third gas reaches a predetermined amount; and a mixing valve having a first inlet port in fluid communication with the first outlet port of the first balancing regulator, a second inlet port in fluid communication with the second outlet port of the first balancing regulator, and a mixing valve outlet port, the mixing valve having two valve seats and an obstruction selectively positionable relative to those valve seats to selectively provide a predetermined flow ratio of each of the gases entering the first and second inlet ports of the mixing valve, the gases passing to the mixing valve outlet port.

2. A device as defined in claim 1, further comprising:
a gas control valve in fluid communication with the third gas supply to selectably control the amount of the third gas passing through the control valve to a second gas outlet;
a gas metering device to determine the amount of the third gas passing through the control valve to the second gas outlet.

3. An apparatus as defined in claim 1, further comprising:
an inter-lock actuated by the selector valve when one of the two gases is selected, the inter-lock selectively cooperating with the bypass valve to prevent passage through the bypass valve of the predetermined gas.

4. An apparatus as defined in claim 3, further comprising:

a second balancing regulator having a first inlet port and a first outlet port in fluid communication, a second inlet port and a second outlet port in fluid communication, the first inlet port of the second balancing regulator being fluidly connected to the first outlet port of the first balancing regulator, the second inlet port of the second balancing regulator being fluidly connected to the second outlet port of the first balancing regulator, the second balancing regulator providing a substantially equal gas pressure at the first and second outlet ports of the second balancing regulator; and wherein
the first inlet port of the mixing valve being in fluid communication with the first outlet port of the second balancing regulator, and the second inlet port of the mixing valve being in fluid communication with the second outlet port of the second balancing regulator.

5. An apparatus as defined in claim 3, further comprising:
visually perceptible indicia cooperating with said mixing valve to indicate the relative amounts of gases being mixed; and
means for changing said indicia as different gases are selected for mixing.

6. An apparatus as defined in claim 4, further comprising:
a resilient member urging at least one of said selector valve or said locking member into a predetermined position to prevent the predetermined gas from passing through said bypass valve.

7. A mixing device for respiratory, therapeutic, or anesthetic uses which provides a gas outlet with a mixture of two gases from three separate pressurized gas supplies containing at least one sustaining gas and one harmful gas, while preventing the patient from inadvertently receiving a flow of harmful gas in the event the supply of the sustaining gas, comprising:
gas selecting means fluidly connected with a first and second gas supplies for selectively providing fluid passage of only one of the first or second gases to a selector outlet port, one of the first or second gas supplies containing a harmful gas;
means for bypassing two of the three gases to the gas outlet;
locking means cooperating with the selecting means and the bypass means for preventing a predetermined one of the first or second gases from being bypassed to the gas outlet;
pressure balancing means fluidly communicating with the selecting means and a third gas supply to substantially equalize the pressures of the gases communicated to the balancing means; and
controllable mixing means in fluid communication with the pressure balancing means and the gas outlet, the mixing means using the pressure of the gasses from the balancing means to controllably select a predetermined ratio of the gasses exiting from the balancing means, the mixing means fluidly providing the ratio of selected gasses to the gas outlet.

8. A mixing device as defined in claim 7 further comprising:
means cooperating with said locking means and said gas selecting means to provide a visual indication of the ratio of gases being mixed and to activate said locking means when said predetermined gas is selected.

9. A mixing device as defined in claim 7 further comprising:
 means cooperating with said locking means and said gas selecting means to provide a visual indication of the relative amounts of gases being mixed, said indicating means changing as different gases are selected for mixing.

10. An apparatus for mixing gases for respiratory or therapeutic use which mixes two gases from three separate pressurized gas supplies containing at least one sustaining gas and one harmful gas while preventing the patient from inadvertently receiving a flow of harmful gas in the event the supply of the sustaining gas inadvertently fails, comprising:
 a first source of a first pressurized gas;
 a second source of a second pressurized gas;
 a third source of a third pressurized gas;
 a selector valve fluidly connected to the first and second gas sources for selectively permitting passage of only one of the first or second gases through the selector valve as a selected gas, one of the first or second gas sources supplying a harmful gas;
 bypass means communicating with the selector valve and the third gas source for providing passage of the third gas or a predetermined one of the first or second gases through the bypass means when the pressure differential at the bypass means between the selected gas and the third gas reaches a predetermined amount:
 a first balancing regulator fluidly connected to the selector valve and the third gas source for substantially equalizing the pressure of the third gas and the selected gas as the gases exit from the first balancing regulator; and
 mixing valve means fluidly connected to the first balancing regulator for providing a predetermined mixture of the third gas and the selected gas to a gas outlet.

11. An apparatus as defined in claim 10 further comprising:
 a second balancing regulator fluidly connected to the first balancing regulator for further equalizing the pressure of the third gas and the selected gas as the gases exit from the second balancing regulator, and wherein the mixing means is fluidly connected to the second balancing regulator.

12. An apparatus as defined in claim 10 further comprising:
 locking means cooperating with the bypass means and the selector valve to prevent passage of the predetermined gas through the bypass means.

13. An apparatus as defined in claim 12, further comprising:
 locking means cooperating with the bypass means to prevent passage of the predetermined gas through the bypass means.

14. An apparatus as defined in claim 13, further comprising:
 gas bypass and metering means fluidly connected to the third gas source for selectively metering an amount of the third gas to a second gas outlet.

15. An apparatus as defined in claim 14 further comprising:
 means cooperating with said locking means and said mixing valve means to provide a visual indication of the ratio of gases being mixed and to activate said locking means when said predetermined gas is selected.

16. A method for mixing two gases from three separate pressurized gas supplies containing at least one sustaining gas and one harmful gas for respiratory, therapeutic or anesthetic use, while preventing the patient from inadvertently receiving a flow of harmful gas in the event the supply of the sustaining gas inadvertently fails, comprising the steps of:
 selecting only one of the first or second gases;
 balancing the pressures of the selected gas and a third gas until they are substantially equal without mixing the gases;
 obtaining a predetermined ratio of the third gas and the selected gas by use of the substantially equal pressures;
 passing the ratioed gases to a gas outlet;
 determining the pressure differential between the third gas and the selected gas;
 bypassing the third gas or a predetermined one of the first or second gases to the gas outlet when the pressure differential reaches a predetermined pressure; and
 activating a locking mechanism simultaneous with the selection of the one of the first or second gases to prevent bypassing of the predetermined one of the first or second gases to the gas outlet.

17. A method for mixing two gases from three separate pressurized gas supplies containing at least one sustaining gas and one harmful gas for respiratory, therapeutic or anesthetic use, while preventing the patient from inadvertently receiving a flow of harmful gas in the event the supply of the sustaining gas inadvertently fails, comprising the steps of:
 selecting one of a first or second gas, at least one of the first or second gases containing the harmful gas;
 balancing the pressures of the selected gas and a third gas until they are substantially equal without mixing the gases;
 obtaining a predetermined ratio of the third gas and the selected gas by use of the substantially equal pressures;
 passing the ratioed gases to a gas outlet; and
 preventing passage of the predetermined one of the first or second gases to the gas outlet when the pressure of the third gas reaches a predetermined pressure.

18. A method as defined in claim 16, comprising the further step of:
 preventing passage of the predetermined one of the first or second gases to the gas outlet when the pressure of the third gas reaches a predetermined pressure.

19. A method as defined in claim 18, comprising the further step of:
 fluidly communicating the third gas source to a second gas bypass in fluid communication with a second gas outlet;
 controlling and metering the third gas as it passes to the second gas outlet.

20. A method as defined in claim 18, comprising the further step of:
 changing scales with the selection of different gases, the scales being calibrated for the various gases selected, said changing step being activated concurrently with the activation of said locking mechanism.

21. A method for mixing gases containing at least one sustaining gas and one harmful gas, comprising the steps of:
    providing a first source of a first pressurized gas, a second source of a second pressurized gas, and a third source of a third pressurized gas, one of said gas sources providing a sustaining gas and at least one of said gas sources providing a harmful gas;
    fluidly communicating the first and second gases to a selector valve, one of the first or second gases containing the harmful gas;
    selectively permitting passage of only one of the first or second gases through the selector valve as a selected gas;
    fluidly communicating the selected gas and the third gas to a first balancing regulator;
    substantially equalizing the pressure of the third gas and the selected gas by passing them through the first balancing regulator;
    fluidly communicating the gases at substantially equal pressures from the first balancing regulator to a mixing chamber;
    controllably selecting the ratio of the selected gas and the third gas entering the mixture chamber by use of the gas pressure;
    fluidly communicating the gases from the mixing chamber to a gas outlet;
    fluidly communicating the selected gas and the third gas to a gas bypass valve;
    activating a safety lock when a particular gas is selected by the selector valve so as to prevent the particular gas from being supplied to the gas outlet through the bypass valve; and
    supplying the third gas to the gas outlet through the bypass valve when the flow rate of the particular gas reaches a predetermined level.

22. A method for mixing gases containing at least one sustaining gas and one harmful gas, comprising the steps of:
    providing a first source of a first pressurized gas, a second source of a second pressurized gas, and a third source of a third pressurized gas;
    fluidly communicating the first and second gases to a selector valve, one of the first or second gases containing a harmful gas;
    selectively permitting passage of only one of the first or second gases through the selector valve as a selected gas;
    fluidly communicating the selected gas and the third gas to a first balancing regulator;
    substantially equalizing the pressure of the third gas and the selected gas by passing them through the first balancing regulator;
    fluidly communicating the gases at substantially equal pressures from the first balancing regulator to a mixing chamber;
    controllably selecting the ratio of the selected gas and the third gas entering the mixture chamber by use of the gas pressure;
    fluidly communicating the gases from the mixing chamber to a gas outlet;
    fluidly communicating the selected gas and the third gas from the first balancing regulator to a second balancing regulator;
    further equalizing the pressure of the third gas and the selected gas by passing them through the second balancing regulator; and
    fluidly communicating the gases from the second balancing regulator to the mixing chamber.

23. A method as defined in claim 22, comprising the further steps of:
    fluidly communicating the third gas to a gas bypass valve;
    controllably metering the amount of the third gas passing through the bypass valve;
    fluidly communicating the metered third gas to a patient.

24. An apparatus as defined in claim 1, wherein said mixing valve further comprising:
    at least two scales calibrated differently to reflect the mixture of the different gases mixed by the mixing valve;
    means for selecting different gases to be placed in fluid communication with said mixing valve and for selecting one of said scales to reflect the mixture of the selected gases.

25. An apparatus as defined in claim 24, further comprising:
    locking means cooperating with said selecting means to prevent a predetermined gas from being passed to a gas outlet.

26. An apparatus as defined in claim 25, further comprising:
    means urging said selecting means to select a gas other than said predetermined gas.

* * * * *